(12) United States Patent
Bruening et al.

(10) Patent No.: US 6,686,479 B2
(45) Date of Patent: Feb. 3, 2004

(54) COMPOSITIONS AND METHODS FOR SELECTIVELY BINDING AMINES OR AMINO ACID ENANTIOMERS OVER THEIR COUNTER-ENANTIOMERS

(75) Inventors: Ronald L. Bruening, American Fork, UT (US); Krzysztof E. Krakowiak, American Fork, UT (US)

(73) Assignee: IBC Advanced Technologies, Inc., American Fork, UT (US)

( * ) Notice: Subject to any disclaimer, the term of this patent is extended or adjusted under 35 U.S.C. 154(b) by 25 days.

(21) Appl. No.: 09/802,123

(22) Filed: Mar. 8, 2001

(65) Prior Publication Data

US 2002/0019491 A1 Feb. 14, 2002

Related U.S. Application Data

(60) Provisional application No. 60/188,935, filed on Mar. 10, 2000.

(51) Int. Cl.[7] .................. C07D 321/00; C09D 323/00; C02F 1/68; C02F 1/00
(52) U.S. Cl. ................. 549/214; 549/348; 210/749; 210/767
(58) Field of Search ................. 549/214, 348; 210/749, 767

(56) References Cited

U.S. PATENT DOCUMENTS

| | | | |
|---|---|---|---|
| 4,001,279 A | 1/1977 | Cram | 549/214 |
| 4,043,979 A | 8/1977 | Cram | 549/214 |
| 4,943,375 A | 7/1990 | Bradshaw et al. | 210/694 |
| 4,952,321 A | 8/1990 | Bradshaw et al. | 210/690 |
| 4,959,153 A | 9/1990 | Bradshaw et al. | 210/610 |
| 4,960,882 A | 10/1990 | Bradshaw et al. | 540/468 |
| 5,071,819 A | 12/1991 | Tarbet et al. | 549/214 |
| 5,078,978 A | 1/1992 | Tarbet et al. | 423/22 |
| 5,084,430 A | 1/1992 | Tarbet et al. | 502/401 |
| 5,173,470 A | 12/1992 | Bruening et al. | 502/401 |
| 5,179,213 A | 1/1993 | Bradshaw et al. | |
| 5,182,251 A | 1/1993 | Bruening et al. | 502/401 |
| 5,190,661 A | 3/1993 | Bruening et al. | 210/670 |
| 5,244,856 A | 9/1993 | Bruening et al. | 502/158 |
| 5,273,660 A | 12/1993 | Bruening et al. | 210/690 |
| 5,393,892 A | 2/1995 | Krakowiak et al. | 549/214 |

OTHER PUBLICATIONS

Jerald S. Bradshaw, et al.; *Enantiomeric Recognition of Organic Ammonium Salts by Chiral Dialkyl–Dialkenyl–, and Tetramethyl–Substituted Pyridino–18–Crown–6 and Tetramethyl–Substituted Bis–Pyridino–18–Crown–6Ligands: Comparison of Temperature–Dependent $^1$H NMR and Empirical Force Field Techniques*[1]; The Journal of Organic Chemistry, 1990, vol. 55; pp. 3129–3137.

Daniel W. Armstrong; *Optical Isomer Separation by Liquid Chromatography*; Analytical Chemistry, vol. 59, No. 2, Jan. 15, 1987; pp. 84A–91A.

Daniel W. Armstrong, et al.; *Macrocyclic Antibiotics as a New Class of Chiral Selectors for Liquid Chromatography*; Analytical Chemistry, vol. 66, No. 9, May 1, 1994; pp. 1473–1484.

Zhang, et al. *Enantiomeric Recognition of Amine Compounds by Chrial Macrocyclic Receptors*; Chemical Reviews, 1997, 97, 3313–3361.

Pirkle WH, et al. *Chiral Stationary Phases for the Direct LC Separation of Enantiomers*; Advances in Chromatography, 1987;27:73–127.

Pirkle, WH, et al.; *Considerations of Chiral Recognition Relevant to the Liquid Chromatographic Separation of Enantiomers*; Chem Rev., 1989, 89: 347–362.

J. Kostrowicki, et al.; *Macrocyclic Polyfunctional Lewis Bases*; Journal of Chromatography, 454 (1988) 340–344.

Primary Examiner—Alan L. Rotman
Assistant Examiner—Raymond Covington
(74) Attorney, Agent, or Firm—Thorpe North & Western, LLP

(57) ABSTRACT

Naphthyl crown ether ligand molecules containing at least two naphthyl groups that are covalently bonded to suitable solid supports and coated by hydrophobic organic solvents are disclosed. These compositions and associated methods are characterized by selectivity of desired amine or amino acid enantiomers over their counter-enantiomers and derivatives. The composition preferably has an α-value greater than or equal to 4. This allows for the separation of such enantiomers with nonchromatographic resin bed separations of three separation stages or less.

17 Claims, No Drawings

COMPOSITIONS AND METHODS FOR SELECTIVELY BINDING AMINES OR AMINO ACID ENANTIOMERS OVER THEIR COUNTER-ENANTIOMERS

RELATED APPLICATIONS

This application claims the benefit of U.S. Provisional Application No. 60/188,935 filed Mar. 10, 2000.

FIELD OF THE INVENTION

The present invention is drawn toward compositions and methods for separating an amine or amino acid enantiomer from its counter-enantiomer in order to obtain a high degree of chiral purity.

BACKGROUND OF THE INVENTION

Effective methods for the separation and recovery of particular enantiomers of biochemicals such as amines and amino acids as well as other types of biochemicals is of great importance in modern technology. This importance is exemplified by the growing need and desire to produce and use optically pure pharmaceuticals and other biochemicals for human and other use. For example, often only one enantiomer of a chemical compound is biologically active or produces a desired effect. Thus, in order for a recipient of a pharmaceutical to receive enough of the biologically active enantiomer, twice the amount of pharmaceutical is generally given (assuming that the enantiomers are represented at about a 50:50 ratio). In other cases, the undesired enantiomer may be toxic or produce side effects. For example, the undesired enantiomer of thalidomide[4] has been known to cause severe malformation in children born to pregnant women who took the drug by prescription for the benefits of the desired enantiomer. Therefore, much research has been conducted in order to produce optically or enantiomerically pure pharmaceuticals such that the biologically active or desired enantiomer may be used in essentially pure forms in order to eliminate the drawbacks discussed above.

There are essentially three theoretical methods that may be used to obtain optically pure compounds for pharmaceutical or other use. First, the desired enantiomer may be synthesized in the desired enantiomeric or optically pure form. Unfortunately this method is often impractical because, in many cases, these types of synthesis methods have not been discovered, or alternatively for those which have been discovered, the production cost of making the pure enantiomer has been prohibitive.

The second method involves separating the desired enantiomer from a mixture containing both enantiomers. However, because the enantiomers differ only in chirality, such processes have proven very difficult to carry out. In some instances, these separations have been accomplished by means of crystallization. For example, tartaric acid as a crystallization platform has been used for such a separation. Though this is a somewhat cost effective method, it is useful in only a minority of cases. In most instances, such separations must be performed using a chromatographic stationary phase and a chromatographic method of separation. However, these type of chromatographic separations have low throughputs and high operating costs.

The third method for chiral separation involves a combination of the two methods described above. In this combination method, an initial chiral intermediate is separated at a relatively high purity followed by additional synthesis steps that further purify the chiral intermediate to a final product without introducing additional chiral impurity. However, with this method, a cost effective chiral separation approach is still needed.

In general, what is often needed to overcome the high cost of performing a chiral separations is to provide a method that allows for high selectivity of the desired enantiomer. As such, in accordance with the present invention, nonchromatographic or equilibrium bind/release separation modes using solid resin phases have been formed to accomplish this result. Before now, solid resin phases of sufficient selectivity and/or stability have not been available to accomplish such an enantiomeric separation function to a degree of purity that is both practical to use and cost effective. This is significant because it is the separation itself that accounts for a large portion of the total cost of making a pure enantiomer product. Thus, by reducing the separation costs, the final selling price of the pure enantiomer may be reduced.

As stated, some research has been done in producing chiral ligands capable of some selectivity between chiral enantiomers of the same compound. Additionally, electrophoresis has been used as well for such chiral separations. However, both of these methods, i.e., chromatography and electrophoresis, provide only low throughputs, and therefore, are not as desired as that described by the present invention. Some articles have described electrophoresis as a separation method and several other articles have discussed the use of such ligands in chromatographic resin phases. Such patents and articles include: U.S. Pat. Nos. 4,001,279 and 4,043,979 issuing to Cram, D. J.; Dotsevi, G., et al., *Chromatographic Optical Resolution through Chiral Complexation of Amino ester Salts by a Host Covalently Bound to Silica Gel, J. Amer. Chem. Soc.,* 97:5, pp 1259–61 (1974); Bradshaw, J. S., et al., *Enantiomeric Recognition of Organic Ammonium Salts by Chiral Dialkyl-, Dialkenyl-, and Tetramethyl-Substituted Pyridino-18-crown-6 and Tetramethyl-Substituted Bis-pyridino-18-crown-6 Ligands: comparison of Temperature-Dependent H NMR and Empirical Force field techniques, J. Org. Chem.,* Volume 55, pp. 3129–37 (1990); Zhang, et al., *Enantiomeric Recoqnition of Amine Compounds by Chiral Macrocyclic Receptors, Chem. Rev.,* Volume 97, pp. 3313–61 (1997); Pirkle, W. H. et al., *Chiral Stationary Phases for the Direct LC Separation of Enantiomers, Adv. Chromatography,* Volume 27, pp. 73–127 (1987); Armstrong, D. W., et al., *Macrocyclic Antibiotics as a New Class of Chiral Selectors for Liquid Chromatoqraphy, Anal. Chem.,* Volume 66, pp. 1473–1484 (1994); Armstrong, D. W., et al., *Optical Isomer Separation by Liquid Chromatoqraphy, Anal. Chem.,* Volume 59, pp. 84A–91A (1987); Huszthy, P., et al., *Entiomeric Separation of Chiral [α-(1-Naphth)Ethyl]Ammonium Perchlorate by Silica Gel-Bound Chiral Pyridino-18-Crown-6 Liqands, Acta Chim Hung,* Volume 131, pp. 445–54 (1994); Pirkle, W. H., et al., *Chem. Rev.,* Volume 89, pp. 347–362 (1989), all of which are incorporated herein by reference.

Specifically, Cram has worked with the naphthyl crown compounds including some attachments to solid supports. However, Cram has only been able to show chromatographic separations with ligand bound solid supports, or alternatively, with coated solid supports. Work to accomplish the high selectivity nonchromatographic separation of amines and amino acids via highly stable covalently attached naphthyl crown ether compounds in three separation stages or less has not been previously demonstrated.

The other references cited above disclose procedures for synthesizing either chromatographic resin materials for chiral separations or for synthesizing unbound ligands with chiral selectivity in single phases. Further, none of the references cited above describe any separations other than chromatographic separations. Therefore, it would be desirable to provide compositions and methods of separating enantiomers using nonchromatographic separation techniques that allow for much faster separations at much higher quantities while maintaining lower cost basis for the separation.

SUMMARY OF THE INVENTION

The present invention is drawn to compositions and methods, the compositions comprising naphthyl crown ether ligand molecules containing at least two naphthyl groups that are covalently bonded to suitable solid supports and coated by hydrophobic organic solvents. These compositions exhibit selectivity of desired amine or amino acid enantiomers over their counter-enantiomers and derivatives. The composition preferably has an α-value greater than or equal to 4 such that one enantiomer is selected over its counter-enantiomer by a factor of 4 or greater. This allows for the separation of such enantiomers with nonchromatographic resin bed separations of three separation stages or less.

Additionally, a nonchromatographic method of separating an enantomeric molecule from its counter-enantiomer is disclosed comprising (a) flowing a feed solution containing a desired enantiomer and its counter-enantiomer through a separation device having a ligand bound to a solid support wherein the ligand has an affinity for the desired enantiomer and a selectivity of at least 4; (b) selectively forming a complex between the desired enantiomer and the ligand thereby forming a first raffinate having increased purity of the counter-enantiomer; (c) breaking the complex between the desired enantiomer and the ligand with a smaller volume of an aqueous receiving solution in which the desired enantiomer is soluble, or which has greater affinity for such desired enantiomer than does the ligand portion of the composition, or which has a greater affinity for the ligand than does the desired enantiomer, thereby quantitatively stripping such desired enantiomer from the ligand and forming a desired enantiomer enhanced receiving liquid; (d) flowing the desired enantiomer enhanced receiving liquid through a separation device having ligands bound to solid supports wherein the ligand has reverse optical activity as compared to the ligand in step (a) such that the ligand has an affinity for the counter-enantiomer; and (e) selectively forming a complex between the counter-enantiomer and the ligand thereby forming a second raffinate having increased purity of the desired enantiomer. This method can be carried out with the compositions disclosed herein, or with any other composition having an affinity for a desired enantiomer over a counter-enantiomer and a selectivity of at least 4.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

"Racemate" or "racemic" when referring to feed solutions is intended to include any solution containing both enantiomeric varieties of a molecule, i.e., the desired enantiomer and counter-enantiomer, in approximate equal amounts. The solution may also contain other matter including other contaminants or impurities that are desired to be separated out.

"Raffinate" is intended to include the solution that passes through the separation device excluding the molecules or enantiomers that bind to the ligands attached to the solid supports. In some instances, the raffinate will contain the desired enantiomer in high concentration and in some instances the raffinate will contain the desired enantiomer in low concentration, depending on whether the ligand is optically designed to bind to the desired enantiomer or the counter-enantiomer.

"Counter-enantiomer," "undesired enantiomer," or "non-desired enantiomer," generally shall include the chiral molecule that is to be separated out from the desired chiral enantiomeric molecule. The term "nondesired" or "undesired" does not mean that these enantiomers are not desirable for any purpose, only that these molecules are undesired to the extent that the other enantiomeric molecule is one the being focused upon for concentration and/or purification.

"Desired enantiomer" or "desired molecule" generally shall include the chiral molecule that the compositions and methods of the present invention are designed to purify, though the counter-enantiomer may desirable in other circumstances or separations.

With these definitions in mind, the invention described herein provides for a sufficiently stable and selective solid resin phase composition and related methods for the separation of desired chiral amines and amino acids from their undesirable enantiomers. Unlike much of the prior art in this area, the separations of the present invention may be carried out utilizing highly desirable and cost effective nonchromatographic separation methods.

The composition is essentially an optically active naphthyl crown ether ligand bonded to a solid support via a covalent bond and then coated with a hydrophobic solvent, thereby forming a highly selective (selectivity factors greater than or equal to 4) nonchromatographic separation resin compound. The compound enables one to separate desired chiral amines, chiral amino acids, and their derivatives from their undesired or counter-enantiomers. The resin compounds of the present invention are highly stable, and thus, may be reused on multiple occasions. Additionally, not only can this composition be used for removing, separating, and/or concentrating certain desired chiral amines or amino acids from their undesired or counter-enantiomers, other impurities as well which may be present may also be separated out.

Specifically, the composition is comprised of at least one ligand covalently bonded to a particulate solid support through a hydrophilic spacer as shown in Formula 1 below:

  Formula 1 where SS is a porous or non-porous particulate inorganic or organic polymer solid support, A is a covalent linkage mechanism, X is a hydrophilic spacer grouping, L is a naphthyl crown ether ligand molecule containing at least two naphthyl groups, and wherein the ligand bound solid support (SS—A—X—L) is coated with a hydrophobic organic solvent with the proviso that when SS is a particulate organic polymer, A—X may be combined as a single covalent linkage. Exemplary hydrophobic solvents that may be used include methylene chloride, chloroform, and/or dichloroethane, though other hydrophobic solvents may be used. Additionally, in the preferred embodiment, L is defined by a structure depicted below in Formula 2:

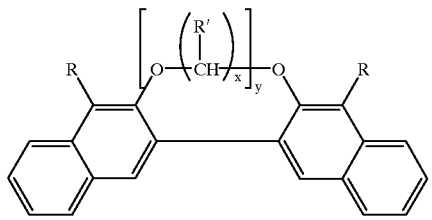

Formula 2 where x is independently from about 2 to 4; y is from about 3 to 8; R is H or preferably a substituted or unsubstituted bulky group independently be selected from the group consisting aliphatic, alicyclic, aromatic, and combinations thereof; and R' is independently selected from the group consisting of hydrogen, lower alkyl having from 1 to 16, glycol, aromatic (including naphthyl and anthracene) with the proviso that at least one R' is functionalized for attachment or attached to SS through the A—X linkage as shown in Formula 1. With respect to R, if the bulky group is aliphatic, from 1 to 16 carbons can be present in saturated and/or unsaturated form and can be a straight or branched chain. With respect to alicyclic, aromatic, and combinations of alicyclic and aromatic, it is preferred that from 1 to 6 ring structures be present. Alicyclic and aromatic rings may also be heterocyclic in that they contain one or more heteroatoms selected from the group consisting of oxygen, sulphur, and nitrogen in the ring structure. Aliphatic groups may also contain oxygen, sulphur and nitrogen atoms within the chain structure to the extent they are functional.

The SS—A—X— portion of Formula 1 is well known for use with ion binding ligands. Preferably solid support "SS" is an inorganic and/or organic particulate support material selected from the group consisting of silica, silica gel, silicates, zirconia, titania, alumina, nickel oxide, glass beads, phenolic resins, polystyrenes and polyacrylates. However, other organic resins or any other hydrophilic organic and/or inorganic support materials meeting the above criteria can also be used. The use of organic ion binding ligands attached to an SS—A—X— solid support by means of a covalent linkage spacer grouping is illustrated in U.S. Pat. Nos. 4,943,375; 4,952,321; 4,959,153; 4,960,882; 5,039,419; 5,071,819; 5,078,978; 5,084,430; 5,173,470; 5,179,213; 5,182,251; 5,190,661; 5,244,856; 5,273,660; and 5,393,892. These patents, which disclose various spacers that can be used in forming an organic ligand attached to a solid support, are incorporated herein by reference.

If an inorganic solid support is used, a hydrophillic spacer is grouped to a silicon, carbon, nitrogen, oxygen, or sulfur atom and is further covalently bonded to a particulate porous and/or nonporous solid support. When the solid support SS is an inorganic material such as silica, silica gel, silicates, zirconia, titania, alumina, nickel oxide, and/or glass beads, the covalent linkage A is a silane such that A—X may be represented by Formula 3 below:

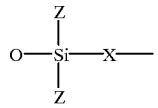

Formula 3 wherein each Z can independently represent members selected from the group consisting of Cl, Br, I, lower alkyl, lower alkoxy, substituted lower alkyl or substituted lower alkoxy and O—SS. As used herein, lower alkyl or lower alkoxy means a group having 1 to 16 carbon atoms. Additionally, X is preferably a spacer grouping having the formula:

$(CH_2)_a(OCH_2CHR^1CH_2)_b$  Formula 4 wherein $R^1$ is a member selected from the group consisting of H, SH, OH, lower alkyl, and aryl; a is an integer from 3 to about 10; and b is an integer of 0 or 1.

If an organic polymer or resin solid support is used, i.e., SS is a particulate polymeric organic solid support matrix such as polyacrylate, polystyrene, and/or polyphenol, the ligand will then generally contain a functional grouping reactive with an activated polar group on the polymer. When the A and X are combined, they may be represented by Formula 5 below:

$—(CH_2)_x—(Y)_y—(CH_2)_z—$  Formula 5 where y is 0 or 1; x and z are independently whole numbers from 0 to 10; and Y is member selected from the group consisting of 0, S, C=N, CO, CONH, CSNH, COO, CSO, NH, NR, SO, $SO_2$, $SO_2NH$, $C_6H_4$, and $CH_2C_6H_4$ where R is lower alkyl with the proviso that at least one of x, y and z must be at least 1.

It is to be emphasized that the present invention does not reside in the discovery of the SS—A—X— portion of Formula 1. Rather, it is the discovery that the optically active naphthyl crown ether ligands covalently bonded to solid supports and coated with a hydrophobic solvent exhibits the ability to nonchromatographically separate enantiomers of chiral amines and/or chiral amino acids.

The preferred method involves utilizing up to three separation stages in a nonchromatographic mode of operation, thus, greatly increasing the product throughput and economic efficiency of any given system despite its size. More particularly, the method for separating such desired amine or amino acid enantiomers from an admixture containing the counter-enantiomer of the chiral amine and/or chiral amino acid (and other non-desired chemicals or particulates) in a common solution is carried out by selectively forming a complex between the desired amine or amino acid enantiomer with the compositions of the present invention described above. These compositions have at least a selectivity factor of 4 in each of up to three separation stages, though one or two separation stages is also functional and within the scope of this invention.

The separation is effectuated by fixing the naphthyl crown ether containing solid support coated with a hydrophobic solvent in a separation device such as a column and flowing the source solution containing a mixture of the two enantiomers of the chiral amine and/or chiral amino acid through the support mass. Specifically, the steps of a preferred method include (1) flowing the admixture containing the desired and counter-enantiomer in a solvent such as water or alcohol through the column packed with the optically active naphthyl containing crown ether ligand solid supported materials coated with a hydrophobic solvent, (2) allowing the ligand to selectively complex with the desired enantiomer, and (3) breaking the complex of the desired enantiomer from the compounds to which the desired enantiomer has become attached by flowing a complex breaking receiving liquid in much smaller volume than the volume of solution originally passed through the column to remove and concentrate the desired enantiomer in solution in the receiving liquid. At this point, the first separation has been effectuated.

Next, the receiving liquid containing a more concentrated amount of the desired enantiomer is then adjusted with solvent addition and/or salt addition to a state where the desired amine or amino acid enantiomers are again capable of binding to the solid supported ligands. The adjusted solution is then run through a separation device containing a naphthyl crown ether ligand of opposite optical or chiral activity bonded to the solid support and coated with a hydrophobic solvent to selectively remove in a nonchromatographic mode a large portion of the remaining counter-enantiomer. Thus, the process of complexation in the second stage is similar to that for the initial separation stage other than the bound ligand used is of the opposite chirality. The second stage may be repeated by again utilizing a ligand of the opposite chirality than that of the first stage such that an even greater purity may be obtained if desired. Whether or not a second or third stage is needed will largely depend on the α-value and desired purity. A reason that it is desirable to conduct the first stage of separation by binding the desired enantiomer to the composition in the separation device is that the counter-enantiomer can be removed along with other undesired chemicals or particulates. If one were to engineer the separation such that the desired enantiomer was obtained in the raffinate after the first stage, then other impurities would remain present with the desired enantiomer. However, though conducting a separation that begins with collecting the desired enantiomer in the raffinate is less desirable from an engineering perspective, it is still within the scope of the present invention.

An α-value of 4.0 indicates a four-fold preference for one enantiomer over its counterpart. Thus, if one is dealing with an α-value of 4.0, then three separations are needed to achieve a 98.5% purity of one enantiomer over the other, assuming a racemic starting solution. Larger α-values lead to either greater purity and/or fewer separation stages. Technologies that can achieve substantial separation in three or less stages can offer significant process benefits both economically and from an engineering perspective. Table 1 below shows a sample of enantiomeric purity obtained as a function of various α-values at various numbers of separation stages for the nonchromatographic system of the present invention, assuming a racemic composition is provided for use in stage one.

TABLE 1

| α-VALUE | NUMBER OF STAGES | PURITY OBTAINED (%) |
|---------|------------------|---------------------|
| 4       | 1                | 80                  |
| 4       | 2                | 94.1                |
| 4       | 3                | 98.5                |
| 6       | 1                | 85.7                |
| 6       | 2                | 97.3                |
| 6       | 3                | 99.5                |
| 8       | 1                | 88.9                |
| 8       | 2                | 98.5                |
| 8       | 3                | 99.8                |
| 10      | 1                | 90.9                |
| 10      | 2                | 99.0                |
| 20      | 1                | 95.2                |
| 20      | 2                | 99.8                |

From this table, it is table, it is apparent that the higher the α-value, the fewer the number of separation stages required to reach 99% enantiomeric purity. For an α-value of 5 (not shown), the use of only three stages allows one to obtain >99% purity.

If desired, the process also allows for recovery of any of the desired amines or amino acids that were not collected during the first stage of separation, i.e., bleed through of the desired enantiomer of the chiral amine and/or chiral amino acid. The solution that remains after most of the desired amine or amino acid has been collected during stage one is called the raffinate. The raffinate containing a minority of the desired amino acid from the initial separation stage may be treated by passing the raffinate through an additional column or columns containing the optically active enantiomer containing crown ether solid supported and coated materials to selectively complex and thus remove a portion of the desired enantiomer from the raffinate. Though it is not required, the use of a smaller enantiomer containing crown ether ligand may be desired to collect the desired amine or amino acids that were not collected during the initial separation stage. Once this is completed, the remainder of the process is similar to the initial separation stage.

Though the compositions and methods describe a preferred system of separation, i.e., three separation stages utilizing ligands of alternating chiralities between the first and second/third stages, other systems may be developed utilizing these principals. For example, one may design the composition such that the undesired or counter-enantiomer in the first column separation is bound to the ligands. Thus, the raffinate would contain the majority of the desired molecular enantiomer, though the use of such a method can leave impurities in the raffinate with the desired enantiomer. To alleviate this, a subsequent stage where the desired enantiomer is bound to the resin can be carried out. These and other combinations of separations are within the scope of the invention. Additionally, the size of the crown ether may be adjusted within the parameters described in order to functionalize or modulate the separation device for maximum efficiency. For example, larger macrocycles can be used for the separation of larger molecules.

Additionally, a nonchromatographic method of separating a desired enantiomer from its counter-enantiomer is disclosed herein that does not necessarily require the ligand bound solid supports of the present invention. With this method, any ligand bound solid support that is optically active or selective of one enantiomer over another may be used. This method comprises (a) flowing a racemate feed solution containing a desired enantiomer and its counter-enantiomer through a separation device having a ligand bound to a solid support wherein the ligand has an affinity for the desired enantiomer over its counter-enantiomer at a selectivity of at least 4; (b) selectively forming a complex between the desired enantiomer and the ligand thereby forming a first raffinate having increased purity of the counter-enantiomer; (c) breaking the complex between the desired enantiomer and the ligand with a smaller volume of an aqueous receiving solution in which the desired enantiomers are soluble, or which has greater affinity for such desired enantiomers than does the ligand portion of the composition, or which has a greater affinity for the ligand than does the desired enantiomers, thereby quantitatively stripping such desired enantiomers from the ligand and forming a desired enantiomer enhanced receiving liquid; (d) flowing the desired enantiomer enhanced receiving liquid through a separation device having ligands bound to solid supports wherein the ligand has reverse optical activity as compared to the ligand in step (a) such that the ligand has an affinity for the counter-enantiomer; and (e) selectively forming a complex between the counter-enantiomer and the ligand thereby forming a second raffinate having increased purity of the desired enantiomer.

Though this method does not require the specific compositions of the present invention, the use of the compositions described herein are highly functional. For example, the ligand bound solid support coated with organic solvent of the present invention have an affinity for desired amine or amino acid enantiomers over their undesired or counter-enantiomer, and thus, are functional within the context of this method.

As stated previously, the composition of the present invention is a naphthyl crown ether ligand having at least two naphthyl groups bound to the solid support. The ligand bound solid support should also be coated with a hydrophobic organic solvent as described herein. Additionally, steps (d) and (e) may be repeated, i.e., a third stage or phase of separation, to increase the purity of the desired enantiomer.

Even the raffinate may be purified by the additional steps of (i) collecting the first raffinate of step (b); (ii) flowing the first raffinate containing a small amount of the desired enantiomer and a large amount of its counter-enantiomer through a separation device having a ligand bound to a solid support wherein the ligand has an affinity for the desired enantiomer and a selectivity of at least 4; (iii) selectively forming a complex between the desired enantiomer and the ligand; (iv) breaking the complex between the desired enantiomer and the ligand forming a racemate feed solution; and (v) repeating steps (a) to (e). Though this method of purifying the raffinate [steps (i)–(v)] is shown in conjunction with the nonchromatographic method of separating a desired enantiomer from its counter-enantiomer [steps (a)–(e)], it is to be noted that steps (i)–(v) may be carried out independently of steps (a)–(e). However, if carried out in conjunction with the nonchromatographic method described in steps (a)–(e), only steps (a)–(b) need to be carried out in order to practice the method shown in steps (i)–(v).

When investigating the suitability of a particular resin-bound separation process, the following factors are often important: (1) resin consumption; (2) solvent usage; (3) productivity, e.g., chemical, optical, and volume yield; (4) total number of separation steps; and (5) capital costs. The nonchromatographic separation method of the present invention compares favorably to current industry practice. For example, the system of the present invention provides reduced number of process steps; high chemical, optical, and volume yields; high feed throughput; more open-ended solvent choice; minimized solvent usage; and low resin consumption.

Reduced number of process steps are achieved in part due to the fact that the ligands of the present invention display both high chemo- and enantio-selectivity, allowing for simultaneous chiral resolution and chemical separation. High chemical, optical, and volume yields are achieved due to the large capacity of the ligands of the present invention for a single enantiomer on each load cycle. The high selectivity also results in high yield throughputs and close to 100% time usage of the system for feed introduction. Additionally, because the ligands of the present invention are bound to solid supports as described, the covalent linkage provides for long life and multiple recycling capabilities. This feature also allows the user to choose the best solvent for the specific results desired, thus, the solvent choice is deemed open ended. Because high feed concentrations can be used and because feeds can be flowed through nearly continuously, the amount of solvent used may be drastically reduced. Also, because of the highly efficient use of the capacity of the ligands bound solid supports as well as their high stability, there is low resin consumption. Conversely, with chromatographic techniques, low yields and high solvent consumption are often realized.

The chiral separations described in the present invention have many possible applications. For example, in the pharmaceutical industry, these separations may be used for analysis, drug development, and commercial production. During the drug discovery process, extensive screening of available compounds is performed along with animal testing. Thus, small quantities of optically pure drug are often needed quickly to screen candidates. Matrix versatility and rapid throughput are often also essential. Additionally, during pre-clinical and clinical development stages, the requirements for optically pure drug quantities can increase dramatically, e.g., from several grams to 100 kilograms. Optically pure drug can also be needed for animal studies, e.g., pharmacokinetics, metabolism, tissue distribution, and safety, and human clinical studies in Phases I, II, and III. Again, time is often critical in these studies, thus, a rapid separation system as described herein would be advantageous. Further, during product launch and production, large amounts of racemate, i.e., >25 tons/year, with total process costs well under the targeted kg drug product price are important to these industries.

Amino acid separation represents another specific application of the present invention. Amino acids are important synthesis precursors (in particular for pharmaceuticals) such as, for example, D-phenylglycine or D-parahydroxyphenylglycine in the preparation of semisynthetic penicillins. They are also used for other chiral fine chemicals and for incorporation into modified biologically active peptides. Since the unnatural amino acids cannot be obtained by fermentation or from natural sources, they must be prepared by conventional synthesis followed by racemate resolution, by asymmetric synthesis, or by biotransformation of chiral or prochiral precursors. Specialized types of amino acids for synthesis applications represent a growing field in the biotechnology industry. Applications include peptide hormones and growth factors, immunologic antigens, enzyme substrates, receptors and ligands, chemical drugs, bioactive peptides for research, combinatorial chemistry, drug discovery, pesticides, and artificial sweeteners, to name a few. Thus, amino acids represent an important class of compounds that can benefit from more efficient separation technologies.

EXAMPLES

The following examples illustrate preferred embodiments of the invention that are presently best known. However, other embodiments can be made and are within the scope of the present invention.

Example 1

Preparation of (R)-3,3'-Dimethyl-2,2'-dihydroxy-1,1'-dinaphthyl

To 18.3 g of sodium hydride was added 50 g (0.175 mol) of 2,2'-dihydroxy-1,1'-dinaphthyl and stirred under nitrogen in 1.0 L of dry tetrahydrofuran (THF). After 1 hour, 116 g of chloromethyl methyl ether was added to the heavy precipitate and the resulting mixture was stirred for about 12 hours and then filtered through a pad of celite. The filtrate was shaken with 500 ml of water and 1 L of methylene chloride. An aqueous layer formed and was extracted two times more with methylene chloride. The combined organic layers were washed with water saturated with potassium bicarbonate. The organic layer was dried and filtered through a squat column of alumina and the column filtrate was evaporated until crystals appeared. The crude product was purified on a silica gel column by elution with a methylene chloride/hexane solution. About 53.5 g (63%) of 2,2'-bis(methoxymethoxy)-1,1'-dinaphthyl, m.p 93–94° C., 0.11 mol was collected.

Next, 171 ml of 1.6 N butyllithium in hexane was added to a mixture of 41 g of the above bisacetal in 1 L of tetrahydrofuran and stirred under nitrogen at 0° C. for 45 minutes. The reaction mixture was then allowed to warm to 25° C. and 25.8 ml of dimethyl sulfate was added to the suspension and the mixture was stirred for 12 hours. About 30 ml of water saturated with sodium carbonate was added and the solvent was evaporated under reduced pressure at 50° C.

The residue, in 300 ml of methylene chloride, was washed twice with water. An additional 300 ml of methylene chloride, 300 ml of methanol, and 25 ml of concentrated hydrochloric acid was added to the organic solution. The solution was stirred for 3 hours, and the solvent was evaporated. The yellow product was recrystallized from methylene chloride-hexane and was purified on a silica gel column (methylene chloride, hexane 1:1) to give 29.5 g (86%) of (R)-3-3'-dimethyl-2,2'-dihydroxy-1,1'-dinaphthyl, m.p. 204–206° C.; $^1$HNMR:2.2(s.6H), 7.1(d.2H), 7.3(m.2H), 7.4 (m.2H), 7.8(m.4H).

Example 2
Preparation of 3,6-dioxa-4-[(allyloxy)methyl)]-1,8-octanediol

About 445 g of glycerol 1-allylether and 1055.5 g of sodium chloroacetate was added to 1056 g of potassium t-butoxide in 10 L of t-butyl alcohol. The mixture was stirred and refluxed for 38 hours and the solvent was removed in a rotary evaporator under vacuum. The residue was dissolved in 2 L of water and the aqueous solution was extracted with ethyl acetate. The water layer was acidified to ph 2 with 6N hydrochloric acid and saturated with a sodium chloride. The water solution was extracted with ethyl acetate (5 L×3). Next, 0.4 kg of anhydrous magnesium sulfate was added after stirring and filtering. The solvent was evaporated on a rotary evaporator and light fraction (up to 130° C./1 mmHg) was removed from the residue. The above residue in 4 L of tetrahydrofuran was added dropwise to the 20 L of tetrahydrofuran with 400 g of lithium aluminum hydride. The reaction mixture was reflexed for 20 hours, cooled, and under argon was added dropwise 2 L of ethyl acetate. The solution was stirred ½ hour and 1 L of water was slowly dropped into the solution. The inorganic salts were filtered after 1 hour of stirring and washed with hot tetrahydrofuran several times. The solvents were evaporated and the residue was distilled under vacuum (125–150° C./0.2 mm Hg). This fraction was distilled again with the column and 600 g of 3,6-dioxa-4-[(allyloxy)methyl]-1,8-octanediol was collected. $^1$HNMR(5), 5.9(m,1H), 5.3(m, 2H), 4.0(m,2H), 3.6 (m,15H).

Example 3
Preparation of 3,6,9,12-tetraoxa-8[(Allyloxy)Methyl]-1,14 Tetradecanediol About 165 g (0.75 mol) of 3,6-dioxa-4-[(alkyloxy) methyl]-1,8-octanediol was dropped under nitrogen to the mixture of 1 L of dimethylformamide and 45 g of sodium hydride under nitrogen. The product was stirred for 1½ hours and 350 g of 2-(2-bromoethoxytetrahydro-2H-pyran was added dropwise. After 48 hours of reflux, the solvent was evaporated. The residue was added to the water and extracted three times with methylene chloride. The combined organic layers were dried with magnesium sulfate, filtered, and evaporated. The residue was distilled under vacuum. A fraction 205°–230° C./0.02 mm Hg was collected. The above fraction was added to a mixture of 300 ml of methylene chloride, 300 ml methanol, and 10 ml hydrochloric acid. This mixture was stirred for 2 days. Sodium bicarbonate was added for neutralization and then evaporated. The residue was distilled under vacuum and collected at 173° C.–193° C./0.05 mmHg. The compound was redistilled with a vigreaux column and collected at 188° C./0.05 mm Hg. About 150 g of 3,6,9,12-tetraoxa-8[(allyloxy) methyl]-1,14-tetradecanediol was collected.

Example 4
Preparation of Ditosylate of 3,6,9,12-tetraoxa-8 [(Allyloxy) Methyl]-1,14-tetradecanediol About 10.2 g of p-toluenesulfonyl chloride in 40 ml tetrahydrofuran was added dropwise at 0°–5° C. to a mixed solution containing 7.7 g of 3,6,9,12-tetraoxa-9[(allyloxy) methyl]-1,14-tetradecanediol in 40 ml of tetrahydrofuran and 3.97 g of sodium hydroxide in 40 ml of water. The above mixture was stirred for 5 hours at a temperature no higher than 5° C. and extracted three times with methylene chloride. The combined organic layers were dried with magnesium sulfate, filtrated, and evaporated. The residue was chromatographed on silica gel with a methylene chloride/ ethyl acetate mixture at a 20:1 ratio. 14.9 g of ditosylate of 3,6,9,2-tetroxa 8[(allyloxy)methyl]-1,14-tetradecanediol was collected as liquid.

Example 5
Preparation of (R)-13[(Allyloxy)Methyl]-2,3,4,5-Bis[1,2-(3-methylnaphto]-1,6,9,12,15,18-hexaoxacycloeicosa-2,4-diene About 23 g (0.202 mol) of potassium t-butoxide was added to a solution of 30 g (0.109 mol) of (R)-3,3$^1$-dimethyl-2,2'-dihydroxy-1,1'-dinaphthyl and 62.0 g (0.101 mol) of ditosylate of 3,6,9,12-tetraoxa-8[(allyloxy)methyl]-1,14-tetradecanediol in 8 L of t-butanol and stirred under nitrogen at 25° C. The mixture was refluxed for 72 hours, cooled, and shaken with 500 ml each of $CHCl_3$ and $H_2O$. The organic layer was dried and evaporated under reduced pressure. The residue was purified on silica gel by elution with hexane and ethyl acetate starting from 50:1 and moving toward solely ethyl acetate. From this, 23.18 g of (R)-[13(allyloxy) methyl]-2,3,4,5-bis[1,2-(3-methylnaphto)]-1,6,9,12,15,18-hexaoxacycloeicosa-2,4-diene was obtained.

Example 6
Preparation of (R)-13-hydroxymethyl-2,3,4,5-Bis[1,2-(3-methylnaphto)]-1,6,9,12,15,18-hexaoxacycloeicosa-2,4-diene To 0.9 g of (R)-13[(allyloxy)methyl]-2,3,4,5-bis[1,2-(3-methylnaphto)]-1,6,9,12,15,18-hexaoxacycloeicosa-2,4-diene in 50 ml of ethanol and 50 ml of $H_2O$ was added 0.06 g of 10% palladium on carbon and 0.2 g of hydrate of p-toluenesulfonic acid and was refluxed for 10 hours. The solution was then filtered. About 10% sodium hydroxide was added to the solution to reach pH 11. The solution solvents were evaporated and the residue was extracted with a chloroform and water mixture three times, the organic layers were combined and dried over magnesium sulfate. The solution solvents were evaporated to give 0.75 g of (R)13-hydroxymethyl-2,3,4,5-Bis[1,2-(3-methylnaphto)]-1, 6,9,12,15,18-hexaoxacycloeicosa-2,4-diene.

Example 7
Attachment of (R)-13-hydroxymethyl-2,3,4,5-Bis[1,2-(3-methylnaphto)]-1,6,9,12,15,18-hexaoxacycloeicosa-2,4-diene Prepared in Example 6 to Chloromethylpolystyrene To 46 g of (R)13-hydroxymethyl-2,3,4,5-Bis[1,2-(3-methylnaphto)]-1,6,9,12,15,18-hexaoxacycloeicase-2,4-diene in 300 ml of tetrahydrofuran was added in 6 g with sodium hydride suspended in 0.4 L of THF dropwise. After 1½ hour, 33 g of the merrifield resin (2 mmole/g of Cl) was added and stirred at reflux for 3 days. Next, about 5 ml of methanol was slowly dropped into the solution. The resin with attached ligand was filtered off and washed with water, methanol, and tetrahydrofuran and then dried at vacuum at about 60° C.

Example 8

Attachment of (R)-13-[(Allyloxy)methyl]-2,3,4,5-Bis[1,2-(3-methylnaphto)]-1,6,9,12,15,18-hexaoxacycloeicosa-2,4-diene Prepared in Example 5 to Silica Gel About 2 g of (R)13-[(allyloxy)methyl]-2,3,4,5-Bis[1,2-(3-methylnaphto)]-1,6,9,12,15,18-hexaoxacycloeicosa-2,4-diene and 10 ml of triethoxysilane were added into a 40 ml volume of toluene.

A few drops of platinum divinyltetramethyl disiloxane complex in xylene was added dropwise and stirred overnight at 60° C. The toluene and excess of triethoxysilane was removed under high vacuum. The residue was added to 1.2 g of 60–100 mesh of silica gel in 50 ml of toluene, heated, and stirred overnight at 80° C. The silica ligand combination was filtered off and washed with toluene.

Example 9

Preparation of (R)-2,2'-dimethoxy-1,1'-dinaphthyl

About 20 g of (R)-2,2'-dihydroxy-1,1'-dinaphthyl and 40 g of potassium carbonate were added to 800 ml of acetone. The mixture was stirred and refluxed overnight. After cooling down, 60 g of methyl iodide was added and refluxed overnight. The slurry was cooled down and about 700 ml of acetone was removed under reduced pressure. To the residue was added about 900 ml of water and the suspension was stirred overnight. The solids were filtered off and dried under vacuum at 80° C. About 20 g of crude (R)-2,2'-dimethoxy-1,1'-dinaphthyl was obtained. An analytical sample was prepared by recrystallization from methylene chloride/benzene m.p 224°–225° C. $^1$HNMR($\delta$), 3.69(s,6H), 7.27 (m.8H), 7.89(m,4H).

Example 10

Preparation of (R)-3,3'-Dibromo-2,2'-dimethoxy-1,1'-dinaphthyl

To a solution of 7.8 g (67 mmole) of tetramethylethylenediamine in 500 ml of ether stirred under nitrogen was added 30 ml (72 mmole) of 2.4 M n-butyllithium in hexane. The mixture was stirred at 25° C. for 15 minutes. Next, 10.0 g (31.8 mole) of (R)-2,2'-dimethoxy-1,1'-dinaphthyl was added and the mixture was stirred for 3 hours. The suspension was cooled to −78° C. and 15 ml (0.3 mole) of bromine in 50 ml of pentane was added over a 10 minute period. The suspension was then warmed to 25° C. and after 4 hours. About 300 ml of a saturated solution of sodium sulfate in water was cautiously added. The mixture was stirred for an additional 4 hours and shaken with 1 L of chloroform and 1 L of water. Layers formed which were then separated. The organic layer was dried and evaporated under reduced pressure and the residue was dissolved in 40 ml of hot benzene. This solution was then added to an alumina column suspended in cyclcohexane. Product was eluted from the column with a cyclohexane-benzene mixture to give the desired crude dibromide. The combined fractions of the mixture were recrystallized from 250 ml of methylene chloride-pentane to give 9 g of (R)-3,3'-Dibromo-2,2'-dimethoxy-1,1'-dinaphthyl m.p. 174–175° C.

Example 11

Preparation of (R)-3,3'-Diphenyl-2,2'-dihydroxy-1,1'-dinaphthyl

To a suspension of 7.7 g (16.3 mmol) of (R)-3,3'-dibromo-2,2'-dimethoxy-1,1'-dinaphthyl and 0.6 g (0.92 mmole) of dichlorobis (triphenylphosphine) nickel (II) in 100 ml of ether stirred under nitrogen was added (after 20 minutes) a solution of 45 mmol of phenylmagnesium bromide in 60 ml of ether. The mixture was refluxed for 20 hours, cooled, and shaken with 600 ml each of chloroform and 1 M hydrochloric acid. The organic layer was dried, evaporated, and dissolved in 50 ml of hot benzene and then chromatographed as 300 g of silica gel suspended in benzene. The combined fractions (~7 g) were dissolved in 600 ml of methylene chloride and cooled to 0° C. About 26 g (96 mol) of tribromoborane was then added. After being stirred for 26 hours at 25° C., the mixture was cooled to 0° C. and the excess of tribromoborane was decomposed by dropwise addition of water. The mixture was shaken with 300 ml of water and the organic layer was dried, concentrated to 30 ml, and chromatographed in 300 g of silica. Washing the column with benzene-ethyl ether gave 4.4 g (63% overall) of (R)-3,3'-diphenyl-2,2'-dihydroxy-1,1'-dinaphthyl. The compound was recrystalized from methylene chloride-cyclohexane m.p. 197°–198° C. $^1$HNMR($\delta$), 5.48(s,2H), 7.6 (m.20H).

Example 12

Preparation of (R)-13-[(Allyloxy)Methyl]-2,3,4,5-Bis[1,2-(3-phenylnaphto)]-1,6,9,12,15,18-hexaoxacycloeicosa-2,4-diene To a solution of 1.1 g (2.3 mmol) of (R)-3,3'-Diphenyl-2,2'-dihydroxy-1,1'-dinaphthyl and 1.65 g (2.7 mmol) of ditosylate of 3,6,9,12-tetraoxa-[8(allyloxy)methyl]-1,14-tetradecanediol in 200 ml of tetrahydrofuran stirred under nitrogen at 25° C. was added 0.36 g (5.5 mmol) of powdered potassium hydroxide. The mixture was refluxed for 72 hours, cooled, and shaken with 500 ml each of chloroform and water. The organic layer was dried and evaporated under reduced pressure and the residue was dissolved in 30 ml of methylene chloride. This material was chromatographed in 150 g of alumina suspended in methylene chloride. Product was eluted from the column with 1 L of methylene chloride and 2 L portions of a methylene chloride-ether mixture to give 0.9 g (56%) (R)13-[(allyloxy)methyl]-2,3,4,5-Bis[1,2-(3-phenylnaphto)]1,6,9,12,15,18-hexaoxacycloeicosa-2,4-diene. $^1$HNMR($\delta$), 3.41(m 20H), 7.64(m.20H).

Example 13

Preparation of (R)-13-hydroxymethyl-2,3,4,5-Bis[1,2-(3-phenylnaphto)]-1,6,9,12,15,18-hexaoxacycloeicosa-2,4-diene To the 0.5 g of (R)-13-allyloxymethyl-2,3,4,5-Bis[2,2-(3-phenylnaphto)]-1,6,9,12,15,18-hexaoxacycloeicosa-2,4-diene in 30 ml of ethanol and 30 ml of water was added 0.2 g of 10% palladium on carbon and 0.036 g of hydrate of p-toluenesulfonic acid and was refluxed 3 days. The solution was then filtered. To the solution, 5% of sodium hydroxide was added to reach ph 11. The solution solvents were evaporated and the residue was extracted with a chloroform and water mixture. The organic layers were combined and dried over magnesium sulfate. The solution solvents were evaporated to give 0.4 g of (R)-13-hydroxymethyl-2,3,4,5-Bis[1,2-(3-phenylnaphto)]-1,6,9,12,15,18-hexaoxacycloeicosa-2,4-diene.

Example 14
Attachment of (R)-13-hydroxymethyl-2,3,4,5-Bis[1,2-(3-phenylnaphto)]-1,6,9,12,15,18-hexaoxacycloeicosa-2,4-diene Prepared in Example 13 to Chloromethylpolystyrene To 0.48 g of (R)-13-hydroxymethyl-2,3,4,5-Bis[1,2-(3-phenylnaphto)]-1,6,9,12,15,18-hexaoxacycloeicosa-2,4-diene in 10 ml tetrahydrofuran was added 53 mg of sodium hydride suspended in 30 ml of tetrahydrofuran dropwise. After ½ hour, 0.6 g of merrifield resin was added and stirred at reflux for 3 days. After cooling, 0.5 ml of methanol was slowly dropped in to the solution. The resin with attached ligand was filtered off and washed with water, methanol, and tetrahydrofuran and dried under vacuum at 60° C.

Example 15
Attachment of (R)-13-[(Allyloxy)Methyl]-2,3,4,5-Bis[1,2-(3-phenylnaphto)]1,6,9,12,15,18-hexaoxacycloeicosa-2,4-diene Prepared in Example 12 to Silica Gel To 0.25 g of (R)13-(allyloxy)methyl-2,3,4,5-Bis[1,2-(3-phenylnaphto)]-1,6,9,12,15,18-hexaoxacycloeicosa-2,4-diene and 3 ml of triethoxysilane were added into 10 ml of toluene. A few drops of a platinum-divinyltetramethyldisiloxane complex in xylene was added dropwise and stirred overnight at 40° C. The toluene and excess of triethoxysilane was removed under high vacuum. The residue was added to 1.2 g of 60–100 mesh silica gel in 50 ml of to toluene and was then heated and stirred overnight at 80° C. The silica/ligand combination was filtered off and washed with toluene.

Example 16
Preparation of (S)-3,3'-Dimethyl-2,2'-dihydroxy-1,1'-dinaphthyl

To 18.3 g of sodium hydride was added 50 g (0.175 mol) of (S)-2,2'-dihydroxy-1,1'-dinaphthyl and stirred under nitrogen in 1.0 L of dry tetrahydrofuran (THF). After 1 hour, 116 g of chloromethyl methyl ether was added to the heavy precipitate and the resulting mixture was stirred for about 12 hours and then filtered through a pad of celite. The filtrate was shaken with 500 ml of water and 1 L of methylene chloride. An aqueous layer formed and was extracted two times more with methylene chloride. The combined organic layers were washed with water saturated with potassium bicarbonate. The organic layer was dried and filtered through a squat column of alumina and the column filtrate was evaporated until crystals appeared. The crude product was purified on a silica gel column by elution with a methylene chloride/hexane solution. About 41 g of (S)-2,2'-bis(methoxymethoxy)-1,1'-dinaphthyl, m.p 93–94° C., 0.11 mol was collected.

Next, 171 ml of 1.6 N butyllithium in hexane was added to a mixture of 41 g of the above bisacetal in 1 L of tetrahydrofuran and stirred under nitrogen at 0° C. for 45 minutes. The reaction mixture was then allowed to warm to 25° C. and 25.8 ml of dimethyl sulfate was added to the suspension and the mixture was stirred for 12 hours. About 30 ml of water saturated with sodium carbonate was added and the solvent was evaporated under reduced pressure at 50° C.

The residue, in 300 ml of methylene chloride, was washed twice with water. An additional 300 ml of methylene chloride, 300 ml of methanol, and 25 ml of concentrated hydrochloric acid was added to the organic solution. The solution was stirred for 3 hours, and the solvent was evaporated. The yellow product was recrystallized from methylene chloride-hexane and was purified on a silica gel column (methylene chloride, hexane 1:1) to give 29.5 g (86%) of (S)-3-3'-dimethyl-2,2'-dihydroxy-1,1'-dinaphthyl, m.p. 204–206° C.; $^1$HNMR:2.2(s.6H), 7.1(d.2H), 7.3(m.2H), 7.4 (m.2H), 7.8(m.4H). This example is comparable to Example 1 except that the starting compound was an (S) enantiomer. Thus, an (S) isomer was formed.

Example 17
Preparation of (S)-13[(Allyloxy)Methyl]-2,3,4,5-Bis[1,2-(3-methylnaphto]-1,6,9,12,15,18-hexaoxacycloeicosa-2,4-diene About 23 g (0.202 mol) of potassium t-butoxide was added to a solution of 30 g (0.109 mol) of (S)-3,3'-dimethyl-2,2'-dihydroxy-1,1'-dinaphthyl and 62.0 g (0.101 mol) of ditosylate of 3,6,9,12-tetraoxa-8[(allyloxy)methyl]-1,14-tetradecanediol in 8 L of t-butanol and stirred under nitrogen at 25° C. The mixture was refluxed for 72 hours, cooled, and shaken with 500 ml each of $CHCl_3$ and $H_2O$. The organic layer was dried and evaporated under reduced pressure. The residue was purified on silica gel by elution with hexane and ethyl acetate starting from 50:1 and moving toward solely ethyl acetate. From this, 23.18 g of (S)-[13(allyloxy)methyl]-2,3,4,5-bis[1,2-(3-methylnaphto)]-1,6,9,12,15,18-hexaoxacycloeicosa-2,4-diene was obtained. This example is comparable to Example 5 with a difference being that the starting compound was an (S) enantiomer. Thus, an (S) isomer was formed.

Example 18
Preparation of (S)-13-hydroxymethyl-2,3,4,5-Bis[1,2-(3-methylnaphto)]-1,6,9,12,15,18-hexaoxacycloeicosa-2,4-diene To 0.9 g of (S)-13[(allyloxy) methyl]-2,3,4,5-bis[1,2-(3-methylnaphto)]-1,6,9,12,15,18-hexaoxacycloeicosa-2,4-diene in 50 ml of ethanol and 50 ml of $H_2O$ was added 0.06 g of 10% palladium on carbon and 0.2 g of hydrate of p-toluenesulfonic acid and was refluxed for 10 hours. The solution was then filtered. About 10% sodium hydroxide was added to the solution to reach pH 11. The solution solvents were evaporated and the residue was extracted with a chloroform and water mixture three times, the organic layers were combined and dried over magnesium sulfate. The solution solvents were evaporated to give 0.75 g of (S)13-hydroxymethyl-2,3,4,5-Bis[1,2-(3-methylnaphto)]-1,6,9,12,15,18-hexaoxacycloeicosa-2,4-diene. This example is comparable to Example 6 except that the starting compound was an (S) enantiomer. Thus, an (S) isomer was formed.

Example 19
Attachment of (S)-13-hydroxymethyl-2,3,4,5-Bis[1,2-(3-methylnaphto)]-1,6,9,12,15,18-hexaoxacycloeicosa-2,4-diene Prepared in Example 18 to Chloromethylpolystyrene To 46 g of (S)13-hydroxymethyl-2,3,4,5-Bis [1,2-(3-methylnaphto)]-1,6,9,12,15,18-hexaoxacycloeicase-2,4-diene in 300 ml of tetrahydrofuran was added in 6 g with sodium hydride suspended in 0.4 L of THF dropwise. After ½ hour, 33 g of the Merrifield resin (2 mmole/g of Cl) was added and stirred at reflux for 3 days. Next, about 5 ml of methanol was slowly dropped into the solution. The resin with attached ligand was filtered off and washed with water, methanol, and tetrahydrofuran and then dried at vacuum at about 60° C. This example is comparable to Example 7 with a difference being that an (S) enantiomer was attached to the chloromethylpolystyrene solid support.

The examples which follow demonstrate how the naphthyl crown ether ligands bonded to solid supports and having a hydrophobic organic solvent coating thereon can be used to remove, concentrate, and/or separate desired enantiomers from counter-enantiomers. The separation is carried out as a composition of the present invention (or other composition having a selectivity of at least 4) having an affinity for the desired enantiomer is placed in a column. An aqueous source solution containing a mixture (usually a racemic mixture) of desired enantiomers and counter-enantiomers is then passed through the column. The flow rate for the solution may be increased by applying pressure with a pump on the top or bottom of the column or applying a vacuum in the receiving vessel. After the source solution has passed through the column and a greater percentage of the counter-enantiomer present in the raffinate is removed, a much smaller volume of a recovery solution (receiving liquid) is used to collect the desired enantiomer in a more purified form. Any receiving solution known by those skilled in the art can be used, provided it is functional with the present invention. This describes a first stage separation. In second or third stage separations, the selectivity of the ligand bound solid support can be reversed such that the desired enantiomer can be collected in the raffinate. Though this is the preferred method, variations can be carried out as would be apparent to one skilled in the art after considering the present disclosure.

The following separation examples are illustrative only and are not comprehensive of the many separations of desired enantiomers over a counter-enantiomers that are possible using the compositions of the present invention.

Example 20
Separation of Enantiomers of Valine Methyl Ester

In this example, 3.9 grams of the dimethyldinaphthyl 20-crown-6 on polystyrene of Example 7 and coated with $CH_2Cl_2$ was placed in each of three columns. A 25° C. 88 ml racemic source solution consisting of 50 mMolar D and L enantiomers of the methyl ester of valine, 0.1 M $HClO_4$, and 3 M $LiClO_4$ was drawn through each of the three columns in series. As is known by those skilled in the art, though three columns are used for this first stage, fewer or more columns may be used to obtained desired results. Next, a 20 ml aqueous solution of 3 M $LiCO_4$ and 0.1 M $HClO_4$ was passed through the column to wash out the loading solution remaining in the three columns. The valine methyl ester loaded on the first column of the three in series was then eluted in 38.9 ml of deionized water at 25° C. as part of a two step process. First, 3.9 ml of water was passed through all three columns to push the contact volume through. Second, 35 ml of additional deionized water was passed through only the first column of the series. The flowrate for all of the separation stages described was about 0.4 ml/min.

The amount of the D and L enantiomer in each of the effluent aqueous aliquots was then analyzed by HPLC. Analyses showed:

1) non-detectable levels of the D valine methyl ester and 4.1 mMolar L valine methyl ester in the 88 ml source solution raffinate which passed through all three columns in series;
2) 0.5 mMolar D valine methyl ester and 25 mMolar L valine methyl ester in the 20 ml wash effluent which passed through all three columns in series;
3) 1.16 mMolar D valine methyl ester and 27 mMolar L valine methyl ester in the 3.9 ml of water which passed through all three columns in series; and
4) 17 mMolar D valine Methyl ester and 2.6 mMolar L valine methyl ester in the 35 ml of deionized water which passed through only the first column.

Hence, the L valine methyl ester which was rejected to form the raffinate by the three columns is quite pure. Additionally, after only a single stage separation, the bound D valine methyl ester gave a purity of about 86.7% (based upon an a-value of >6).

The Example thus far describes only the first stage of up to three separation stages. If the desire is to further purify the L valine methyl ester or the D valine methyl ester, additional stages can be performed. For example, the D valine methyl ester can be further purified to 97% and even to >99% if a second or third stage of the separation is performed, respectively. To accomplish this, once the D valine methyl ester bound to the compositions within the separation device is contacted with the aqueous receiving solution, the additional separation stages are carried out. Specifically, the receiving solution containing much more D valine methyl ester (about 86.7%) than L valine methyl ester is preferably ran through a column or other separation device that is configured such that the resin may selectively bind to the minority of L valine methyl ester. This is done by reversing the chirality of the ligand by using the resin material described in Example 19 instead of the resin material described in Example 7. Thus, after only this second stage, the resin, i.e., coated ligand bound solid support, binds to the L valine methyl ester producing a raffinate containing about 97% pure D valine methyl ester (based upon an α-value >6). If a third stage separation is desired, the raffinate of stage two is run through a separation device similar to that describe in stage two, purifying the third stage raffinate to >99% D valine methyl ester.

Example 21
Separation of Enantiomers of Phenylalanine

In this example, columns containing 3.9 gram of the dimethyldinaphthyl 20-crown-6 ligands bonded to polystyrene solid supports were prepared as described in Example 7 and then were coated with $CH_2Cl_2$. Separations were carried out similar to those described in Example 20, except that the 25° C. racemic source solution contained 37.5 mMolar D and L enantiomers of the amino acid phenylalanine (instead of methyl ester of valine as described in Example 21).

After carrying out the first stage separation, HPLC analysis of the receiving solution showed that 89% of D-phenylalanine (as compared to 11% of L-phenylalanine) was bound to the ligand and ultimately separated. Thus, after the first stage separation, the selectivity or α-value was calculated to be about 8.5.

Further purification was carried out by preparing a column with the composition described in Example 19 and coating the composition with $CH_2Cl_2$ (rather than the composition of Example 7). This coated composition was placed in a separation device and the receiving solution (from stage one) containing much more D-phenylalanine (89%) was ran through the column containing the resin of Example 19 (reverse chirality compared to Example 7) such that the L-enantiomer primarily bound to the solid support. As a result, the raffinate contained the further purified concentration of the desired enantiomer. Thus, after only two separation stages, the raffinate of the second stage produced a D-phenylalanine composition that was 98.6% pure. A third separation, similar to the second separation, can also be carried out if further purification is desired.

While the invention has been described with reference to certain preferred embodiments, those skilled in the art will appreciate that various modifications, changes, omissions, and substitutions can be made without departing from the spirit of the invention. For example, though it is preferred that the desired enantiomer be collected at the first stage in the receiving solution, and at the subsequent stages in the raffinate, at any given stage, the separation device can be engineered such that the raffinate or the receiving solution contains the desired enantiomer. It is intended, therefore, that the invention be limited only by the scope of the following claims and equivalents thereof.

What is claimed is:

1. A method for concentrating, removing, and separating an amine or amino acid enantiomer from its counter-enantiomer from a source solution containing an enantiomeric mixture comprising the steps of:

(a) contacting the source solution having a first volume with a composition comprising at least one ligand covalently bonded to a particulate solid support through a hydrophilic spacer having the formula:

SS—A—X—L wherein SS is a porous or non-porous particulate inorganic or organic polymer solid support, A is a covalent linkage mechanism, X is a hydrophilic spacer grouping, L is a bisnaphthyl crown ether ligand molecule having at least two naphthyl groups, wherein SS—A—X—L is coated with a hydrophobic organic solvent with the proviso that when SS is a particulate organic polymer, A—X may be combined as a single covalent linkage, and wherein the L portion of the composition has an affinity for a desired amine or amino acid enantiomer over its counter-enantiomer such as to form a complex between the desired amine or amino acid enantiomer and the ligand;

(b) removing the source solution from contact with the composition to which the desired amine or amino acid enantiomer has been complexed;

(c) contacting the composition having the desired amine or amino acid enantiomer complexed thereto with a smaller volume of an aqueous receiving solution in which the desired amine or amino acid enantiomer is soluble, or which has greater affinity for such desired amine or amino acid enantiomer than does the ligand portion of the composition, or which has a greater affinity for the ligand than does the desired amine or amino acid enantiomer, thereby quantitatively stripping such desired amine or amino acid enantiomer from the ligand; and (d) recovering the desired amine or amino acid enantiomer in concentrated form in the receiving solution.

2. A method as in claim 1 wherein L has the formula:

$$R\underset{}{\overset{}{\bigotimes}}\left[O-\left(CH\underset{R'}{}\right)_x-O\right]_y R$$

where x is independently from about 2 to 4; y is from about 3 to 6; R is independently H or a substituted or unsubstituted bulky group independently selected from the group consisting of aliphatic, alicyclic, aromatic, and combinations thereof; and R' is independently selected from the group consisting of hydrogen, lower alkyl, glycol, and aromatic with the proviso that at least one R' is functionalized for attachment or attached to SS by A—X.

3. A method as in claim 1 wherein SS is an inorganic solid support selected from the group consisting of sand, silica gel, glass, glass fibers, alumina, zirconia, titania, nickel oxide and combinations thereof.

4. A method as in claim 1 wherein A is Si(Z,Z)—O, wherein Z can independently represent members selected from the group consisting of Cl, Br, I, lower alkyl, lower alkoxy, substituted lower alkyl or substituted lower alkoxy and O—SS.

5. A method as in claim 1 wherein X is represented by the formula:

$(CH_2)_a(OCH_2CHR—CH_2)_b$ wherein $R^1$ is a member selected from the group consisting of H, SH, OH, lower alkyl, and aryl; a is an integer from 3 to about 10; and b is an integer of 0 or 1.

6. A method as in claim 1 wherein SS is a particulate polymeric organic solid support matrix selected from the group consisting of polyacrylate, polystyrene, and polyphenol and combinations thereof.

7. A method as in claim 1 wherein A and X combined are represented by the formula:

—$(CH_2)_x$—$(Y)_y$—$(CH_2)_z$— where y is an integer of 0 or 1; x and z are independently integers between 0 and 10; and Y is member selected from the group consisting of O, S, C=N, CO, CONH, CSNH, COO, CSO, NH, NR, SO, $SO_2$, $SO_2NH$, $C_6H_4$ and $CH_2C_6H_4$ where R is lower alkyl with the proviso that at least one of x, y and z must be at least 1.

8. A nonchromatographic method of separating an enantomeric molecule from its counter-enantiomer comprising:

(a) flowing a feed solution containing a desired enantiomer and its counter-enantiomer through a separation device having a ligand bound to a solid support wherein the ligand has an affinity for the desired enantiomer and a selectivity of at least 4;

(b) selectively forming a complex between the desired enantiomer and the ligand thereby forming a first raffinate having increased purity of the counter-enantiomer;

(c) breaking the complex between the desired enantiomer and the ligand with a smaller volume of an aqueous receiving solution in which the desired enantiomer is soluble, or which has greater affinity for such desired enantiomer than does the ligand portion of the composition, or which has a greater affinity for the ligand than does the desired enantiomer, thereby quantitatively stripping such desired enantiomer from the ligand and forming a desired enantiomer enhanced receiving liquid;

(d) flowing the desired enantiomer enhanced receiving liquid through a separation device having ligands bound to solid supports wherein the ligand has reverse optical activity as compared to the ligand in step (a) such that the ligand has an affinity for the counter-enantiomer; and (e) selectively forming a complex between the counter-enantiomer and the ligand thereby forming a second raffinate having increased purity of the desired enantiomer.

9. A method as in claim 8 wherein the ligand of step (a) has an affinity for a desired amine or amino acid enantiomer over its counter-enantiomer.

10. A method as in claim 8 wherein the ligand of step (d) has an affinity for a counter-enantiomer of an amine or amino acid.

11. A method as in claim 8 wherein the ligand bound to the solid support is a naphthyl crown ether having at least two naphthyl groups, and wherein the naphthyl crown ether bound to the solid support is coated with a hydrophobic organic solvent.

12. A method as in claim 8 further comprising repeating steps (d) and (e).

13. A method as in claim 8 further comprising the steps of:
   (i) collecting the first raffinate;
   (ii) flowing the raffinate containing a smaller amount of the desired enantiomer and a larger amount of its counter-enantiomer through a separation device having a ligand bound to a solid support wherein the ligand has an affinity for the desired enantiomer and a selectivity of at least 4;
   (iii) selectively forming a complex between the desired enantiomer and the ligand; and
   (iv) breaking the complex between the desired enantiomer and the ligand forming a racemate feed solution.

14. A method as in claim 13 wherein after steps (i) to (iv) are completed, steps (a) to (c) are repeated.

15. A method as in claim 14 wherein after steps (a) to (c) are completed, steps (d) and (e) are repeated.

16. A method as in claim 8 wherein the feed solution is racemic.

17. A method as in claim 1 wherein the hydrophobic organic solvent is selected from the group consisting of methylene chloride, chloroform, dichloroethane, and combinations thereof.

* * * * *